(12) United States Patent
Rodak et al.

(10) Patent No.: US 8,674,142 B2
(45) Date of Patent: Mar. 18, 2014

(54) NAPHTHENIC HYDROCARBON ADDITIVES FOR DIARYL PHOSPHIDE SALT FORMATION

(75) Inventors: Nicholas J. Rodak, Princeton, NJ (US); Gary S. Silverman, Chadds Ford, PA (US); Stephen W. Carson, Coatesville, PA (US)

(73) Assignee: PMC Organometallix, Inc., Wilmington, DE (US)

( * ) Notice: Subject to any disclaimer, the term of this patent is extended or adjusted under 35 U.S.C. 154(b) by 571 days.

(21) Appl. No.: 12/721,885

(22) Filed: Mar. 11, 2010

(65) Prior Publication Data

US 2010/0234642 A1  Sep. 16, 2010

Related U.S. Application Data

(60) Provisional application No. 61/159,615, filed on Mar. 12, 2009.

(51) Int. Cl.
  *B01J 31/02* (2006.01)
  *B01J 23/04* (2006.01)
  *B01J 31/06* (2006.01)
  *C07F 9/02* (2006.01)

(52) U.S. Cl.
  USPC ............ 568/17; 502/173; 502/152; 502/159; 568/588

(58) Field of Classification Search
  None
  See application file for complete search history.

(56) References Cited

U.S. PATENT DOCUMENTS

| | | |
|---|---|---|
| 5,654,486 A | 8/1997 | Senaratne et al. |
| 5,710,340 A | 1/1998 | Senaratne |
| 5,777,169 A | 7/1998 | Layman, Jr. et al. |
| 5,866,720 A | 2/1999 | Layman, Jr. et al. |
| 2008/0194103 A1* | 8/2008 | Wagner .................. 438/680 |
| 2008/0242791 A1* | 10/2008 | Callais et al. ............ 524/492 |
| 2010/0197816 A1* | 8/2010 | Goldbach et al. ........... 521/27 |

OTHER PUBLICATIONS

Yamamoto, T. "Electrochemical reduction potential of n-type pi-conjugated polymers," J. Polymer Sci. A. (1996) 34; 997-1001.*
Olah, G., Hehemann, D., "Friedel—Crafts Type Preparation of Triphenylphosphine", J. Org. Chem., vol. 42, No. 12, 1977, p. 2190.
Chou, T., et al., "Ultrasound in Phosphine Preparation. Simple Preparations of Some Bis(alkylphenylphosphino)alkanes", J. Org. Chem. 1985, 50, p. 4329-4332.
Chou, T., et al., "Cleavage of Phosphorus-Carbon Bonds with Sodium/Naphthalene, Facile Preparation of Unsymmetrical Diphosphines", Journal of Organometallic Chemistry, 312 (1986), p. 53-58.
Toth, I., et al., Aspects of the Cleavage of Phosphines with Potassium: Synthesis and Reactivity of Lithium and Potassium Bis (p-(dimethylamina) phenyl) phosphide, Organometallics 1990, 9, p. 675-680.
Wittenberg, D., et al., "Lithium Cleavages of Triphenyl Derivatives of Some Group Vb Elements in Tetrahydrofuran", J. Org. Chem. 1958, p. 1063-1065.

* cited by examiner

*Primary Examiner* — Johann R Richter
*Assistant Examiner* — Mark Luderer
(74) *Attorney, Agent, or Firm* — Blank Rome LLP (57) ABSTRACT

The invention relates to the use of polycyclic aromatic hydrocarbons (PAHs) such as naphthalene and its alkyl, aryl, or heteroatom substituted analogs, that act as catalysts in the presence of an alkali metal (Li, K, Na) for the reduction of electron-deficient and electron-rich triaryl phosphines to their corresponding alkali metal diaryl phosphide salts. The process is also useful for the catalysis of triaryl phosphine chalcogen adducts such as the sulfides, oxides, and selenides, diaryl(halo)phosphines, triaryl phosphine-borane adducts, and tetra-aryl bis(phosphines) that can also be reduced to their corresponding alkali metal diaryl phosphide salts. The invention also relates to small molecule PAHs and polymer tethered PAHs naphthenics.

4 Claims, 2 Drawing Sheets

NAPHTHENIC HYDROCARBON ADDITIVES FOR DIARYL PHOSPHIDE SALT FORMATION

FIELD OF THE INVENTION

The invention relates to the use of polycyclic aromatic hydrocarbons (PAHs) such as naphthalene and its alkyl, aryl, or heteroatom substituted analogs, that act as catalysts in the presence of an alkali metal (Li, K, Na) for the reduction of electron-deficient and electron-rich triaryl phosphines to their corresponding alkali metal diaryl phosphide salts. The process is also useful for the catalysis of triaryl phosphine chalcogen adducts such as the sulfides, oxides, and selenides, diaryl(halo)phosphines, triaryl phosphine-borane adducts, and tetra-aryl bis(phosphines) that can also be reduced to their corresponding alkali metal diaryl phosphide salts. The invention also relates to small molecule PAHs and polymer tethered PAHs naphthenics.

BACKGROUND OF THE INVENTION

The formation of diaryl phosphide salts from triaryl phosphine and triarylphosphine adducts is an important commercial process. Alkali metal diaryl phosphide salts are used as synthetic intermediates in the synthesis or manufacture of various mono-substituted diaryl phosphines, and complex phosphine ligands for organometallic catalysts as well as phosphine derivatives for various other applications such as phase transfer catalysis, epoxy curing agents, or flame retardants.

There are currently several methods by which this reduction is accomplished. Lithium metal cleavage of triphenyl phosphine to lithium diphenyl phosphide occurs in THF at 25° C. However, lithium diaryl phosphides interact and react with ethereal solvent thus facilitating its decomposition, tend to lead to a loss or decrease in substituted diaryl phosphine product yield and purities, are less reactive due to greater P-M bond covalency (M=Li), and additionally, lithium metal is less desirable due to greater cost and need for argon atmosphere to prevent hazardous lithium nitride formation.

Potassium metal can also be used as the alkali metal reductant alone, without the need for catalyst, to react with triaryl phosphines and its derivatives under typical useful conditions, but again is prone to side reactions, i.e. alkyl halide decomposition that tend to lead to a loss or decrease in substituted diaryl phosphine product yield and purities. Moreover, use of lithium and potassium alkali metals can give rise to significant aryl group scrambling on either the phosphine and phosphide species, i.e. they have low specificity for $Ar_2PPh$, $(Ar')ArPPh$, etc. derived from mixed aryl phosphine precursors, which is especially true for lithium metal.

Sodium by itself or with previously reported additives such as amines is reported to insufficiently cleave electron rich phosphines since it is reported to possess a reducing capacity for phosphines that is significantly lower than that of either lithium or potassium. (Schmidt, U.; Kabitzke, K. Markau, K.; Muller, A. Chemische Berichte 1966, 99, 1497). Therefore sodium by itself is not a preferred alkali metal for this use. On the other hand, sodium is a cost effective alternative to lithium and potassium, is easily handled on a large scale, and does not facilitate deleterious phoshine aryl group scrambling. Therefore, from a cost and commercial synthetic perspective, sodium is a more desirable alkali metal reductant.

U.S. Pat. No. 5,866,720 and U.S. Pat. No. 5,777,169 disclose the reduction of triarylphosphine in the presence of molecular hydrogen in an "anhydrous organic liquid diluent." The organic diluent is paraffinic, cylcoparaffinic, or aromatic hydrocarbon based, preferably THF. Non-alkylated naphthenics and amine catalysts may be present without deleterious effects.

U.S. Pat. No. 5,710,340 discloses a process for forming cycloalkyldiarylphosphines from triarylphosphines using sodium or potassium. THF is the preferred solvent.

Olah and Hehemann, J. Org. Chem., Vol. 42, No 12, 1977, p 2190 describe the reduction of triphenyl phosphine sulfide ($Ph_3P=S$) to triphenyl phosphine ($Ph_3P$) by charging stoichiometric sodium naphthalenide complex. The authors did not contemplate continuing the exposure of the triphenyl phosphine to more sodium naphthalenide or alkali metal (if used in excess relative to naphthalene) to produce further, quantitative conversion to the sodium diphenyl phosphide salt.

Surprisingly, it has now been found that the reducing activity of sodium may be boosted and facilitated by the formation of polycyclic aromatic hydrocarbon (PAH) radical anion reductants to prepare alkali metal diaryl phosphide salts from both electron rich-, deficient-, and mixed triaryl phosphines on acceptable manufacturing timescales.

The cleavage of triaryl phosphines and their relevant derivatives to their corresponding alkali metal diaryl phosphide salts was found to readily occur with sodium metal in tetrahydrofuran at 55° C. in the presence of various dissolving alkali metal polycyclic aromatic hydrocarbons (naphthenic additives). Specifically, the polycyclic aromatic hydrocarbons employed may be of three forms: a perhydrotreated naphthenic oil by-product or distillate of specific identity, a discrete small molecule such as naphthalene or its (per)alkylated and/or heteroatom-containing analog, or a (co)polymer supported form in which the PAH catalytic unit is incorporated either in the main chain or as a pendant group.

Specific examples of active polycyclic aromatic hydrocarbons include perhydrotreated naphthenic oils, naphthalene, [1-methyl]naphthalene, and 1-[N,N-dimethylamino]naphthalene, and/or homo- or copolymers containing the naphthenic unit in any of its indicated substituted derivatives as either a pendant or main chain unit or a combination thereof. Some or all of the PAH catalyst may be reduced to an unreactive x,y-dihydro-derivative that must be separated from the finished product.

Further, with the use of appropriate separation techniques, each of these PAH forms of catalyst can be readily and effectively removed from the process prior to crystallization.

SUMMARY OF THE INVENTION

The invention relates to a catalytic dispersion for the reduction of triaryl phosphines comprising an alkali metal dispersed in a polycyclic aromatic hydrocarbon, wherein said polycyclic aromatic hydrocarbon is a small molecule alkylated naphthenic, or a polymer supported naphthenic.

The invention further relates to a process for the reduction of triaryl phosphide to diaryl phosphide comprising the steps of:
  a) admixing triaryl phosphine with a polycyclic aromatic hydrocarbon (PAH) and an effective amount of alkali metal to form a reaction mixture; and
  b) reacting said reaction mixture to form diaryl phosphide alkali salt,
wherein said polycyclic aromatic hydrocarbon is a small molecule alkylated naphthenic, or a polymer supported naphthenic.

DETAILED DESCRIPTION OF THE INVENTION

Figure 1:
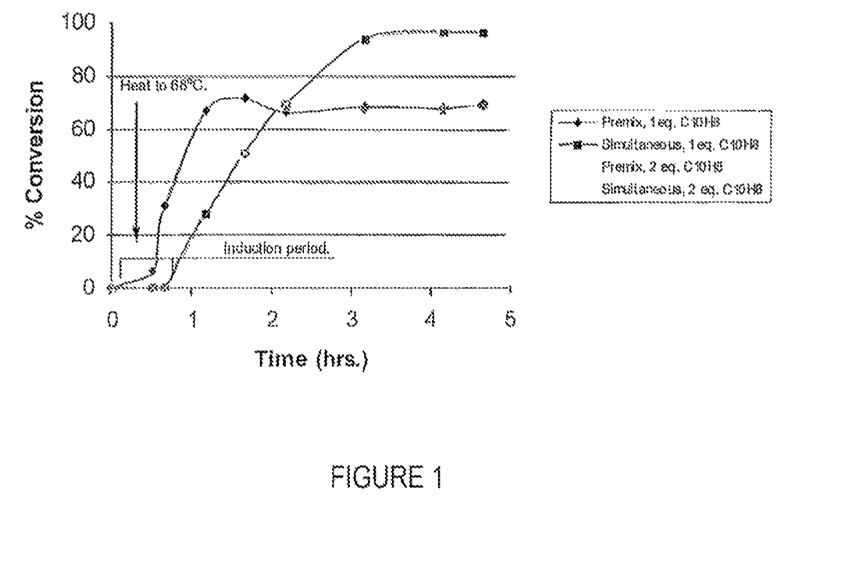
FIG. 1: Is a kinetic analysis plot of tris[3,5-xylyl]phosphine reduction using sodium naphthalenide. Induction period involves heating the reaction mixture from 25° C. to 68° C. under N, atmosphere.
Figure 2:
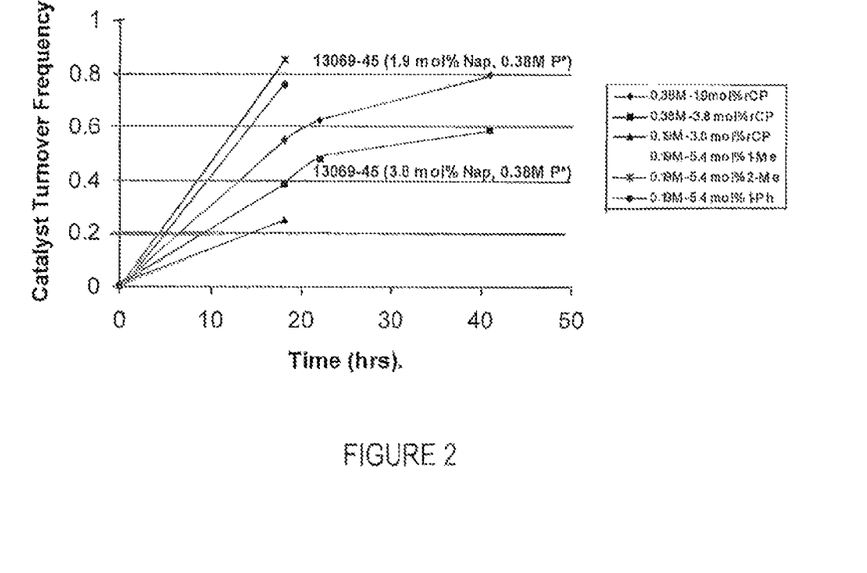
FIG. 2: Is a plot of the data from Table 7 showing the PAHC catalyst turnover frequencies of catalysts of the invention. PAHC represents the polycyclic aromatic hydrocarbon, either as small molecules or supported on a styrenic copolymer as indicated. SNC 2 is the random copolymer of styrene and the monomer 4-[1-naphthyl-CH$_2$CH$_2$OCH$_2$]styrene 3 prepared by CRP using BlocBuilder®. The 1-Me, 2-Me, and 1-Ph represent [1-methyl]naphthalene, [2-methyl]naphthalene, and [1-phenyl]naphthalene, respectively. The x mol % Nap represents C10H7 charged as polymer supported and P* represents the concentration of (3,5-xylyl)$_3$P in THF.

The invention relates to the cleavage of triaryl phosphines and their relevant derivatives to the corresponding alkali metal diaryl phosphide salts in the presence of various dissolving alkali metal polycyclic aromatic hydrocarbon, (naphthenic additives). Specifically, the polycyclic aromatic hydrocarbons employed may be of three forms: a perhydrotreated naphthenic oil by-product or distillate of specific identity, a discrete small molecule such as naphthalene or its (per)alkylated and/or heteroatome containing analogs, or a (co)polymer supported form in which the PAH catalytic unit is incorporated either in the main chain or as a pendant group.

the polycyclic aromatic hydrocarbons serve to solubilize the solid alkali metals, and in the process form a radical anionic species capable of facilitating the homogeneous reduction of said phosphine derivatives to corresponding sodium diaryl phosphide salts. The intermediate product diaryl phosphide, or "phosphide" can then be reacted with a variety of electrophiles such as alkyl halides to give rise to value-added, substituted trivalent phosphine derivatives for various applications. The preferred conditions include the use of sodium metal and cyclic ethereal solvents such as THF from ambient to elevated temperatures, i.e. reflux under inert atmosphere conditions. In its simplest form, the phosphine, the PAH catalyst, and solid sodium metal cubes are charged to an inert reactor and degassed with a rapid N$_2$ flow. Then, THF is added and the contents heated to 55° C. under the N$_2$ atmosphere for a period of time sufficient to bring about quantitative reduction of said phosphine derivatives to the corresponding sodium diaryl phosphide. The preferred temperature range is 40-60° C. The progress of the reaction can easily be monitored using 31P NMR analyses of sequential reaction mixture aliquots.

Diagram 1

General Process

The process of the invention involves the cleavage of triaryl phosphines and their relevant derivatives in the presence of alkali metal polycyclic aromatic hydrocarbons (PAH) to the corresponding alkali metal diaryl phosphide salt. The overall transformation can be best explained as a net two-electron transfer mechanism as shown schematically in Diagram 1 below.

The PAH-derived alkali metal aromatic radical anion catalyzed reduction reactions are general in nature and quantitative and occurring with extremely high selectivity and sufficient rates under industrially feasible conditions. Specifically, Phosphines:

The starting material can be a mono aryl, diaryl, triaryl phosphine or there relevant derivatives and substituted R groups. These include, in order of highest to lowest preference, tertiary aryl phosphines, bis(phosphines), i.e. Ar$_2$P—PAr$_2$, aryl/alkyl halo-phosphines, zwitterionic triaryl phosphine-borane complexes (Ar3P->BH3), chalcogen containing phosphines (O, S, Se), and secondary phosphine, or chlorodiaryl phosphines. Diagrams 2 and 3 illustrate the reduction of tris[3,5-xylyl]phosphine, 3,5-TXP, to the corresponding bis[3,5-xylyl]phosphide salt with successful conversion to either bis[3,5-xylyl]PBu, a mono-substituted diaryl phosphine (Diagram 2) or a 1,4-bis(phosphine) derivative of the DIOP ligand (Diagram 3) as shown in the attachment Diagram 2, Monophosphine:

Diagram 3, Bisphosphine:

alkyl/aryl mesylates, alkyl/aryl tosylates, epoxides, thioepoxides, aziridines, para-nitrophenoxides, or the like.

Solvents:

Solvents useful in the reaction include, but are not limited to, cyclic ethers such as THF, (2-Me)THF, 1,3-dioxane, 1,4-dioxane, 2-methyl-1,3-dioxolane, dioxolane; linear ethers such as diethyl ether, dibutyl ether, 1,2-dimethoxyethane, 1,2-diethoxyethane, 1,2-dimethoxypropane, 1,3-dimethoxypropane or any combination thereof.

Metals:

The alkali metals Li, K, Na, Cs, and Fr may all in theory be used in the reaction. Preferred metals are Na, K, and then Li, in that order, the most preferred being Na. Processes that employ either lithium or potassium as the reducing alkali metal may suffer from several deleterious side reactions, including but not limited to, solvent degradation, product "phosphide" aryl group scrambling, alkyl halide or tosylate degradation, reduced phosphide reactivity, etc. that do not occur when sodium is employed. In the presence of the disclosed PAH catalysts sodium possesses a sufficient and significant reactivity to effect the quantitative and selective reduction of said phosphine derivatives to the corresponding sodium diaryl phosphide salts on acceptable manufacturing timescales. In one preferred embodiment, a blend of Na and K is used.

For the Na dispersion in naphthenic oil the typical level of the Na is 5-45 wt %, preferably 15-40 wt %, and most preferably 30-40 wt %. The dispersion can be prepared by any means known to those skilled in the art of preparing alkali metal dispersions in these perhydrotreated naphthenic oils. Additives, such as oleic acid, may also be added in <2.5 wt % of the oil dispersion to stabilize the dispersion without deleterious effects on the rate or selectivity of the reduction of the triaryl phosphine derivative to the corresponding diaryl phosphide.

Coupling Agents:

Useful coupling agents for use in the reaction include, but are not limited to alkyl/aryl chlorides, alkyl/aryl bromides, Polycyclic Aromatic Hydrocarbon (PAH)

The polycyclic aromatic hydrocarbons employed may be of three forms: a perhydrotreated naphthenic oil by-product or distillate; a discrete small molecule PAH such as naphthalene or its (per)alkylated analogs and/or its heteroatom-bearing analogs; or a polymer supported naphthenic in which the PAH catalytic unit is incorporated either in the main chain or the pendant group or a combination thereof and without any regard to specific placement relative to each other.

The choice of the specific PAH to use in a specific reaction may be based on factors such as ease of preparation, enhanced triaryl phosphine reducing reactivity or rates, prevention or suppression of product mono-substituted diaryl phosphine over-reduction, and ease of spent PAH removal from the mono-substituted diaryl phosphine product.

Naphthenic Oils

Perhydrotreated naphthenic oil by-product or distillates, specifically identified by their CAS #s 64742-53-6 and 664742-52-5, are useful for the dispersion of the alkali metals and to facilitate diaryl phosphide formation. A particularly useful dispersion is sodium metal dispersed in the CAS#64742-53-6 and 664742-52-5 oils. Useful oils are shown in Table 2. The particle sizes in the Table are of the dispersions prepared from molten sodium in the perhydrotreated naphthenic using a high speed, high shear blending unit. The smaller the particle size, the faster the reaction due to a greater surface area. Note with the use of the dispersions for the reduction there is an internal competition between sodium reaction with the phosphine and sodium agglomeration to give larger, less reactive particles due to a lower surface area:volume ratio.

Several paraffinic, or saturated hydrocarbon oils were evaluated and were found not able to form stable sodium dispersions in useful wt % regions, even with the addition of oleic acid, a common dispersion stabilizer. Moreover, all such paraffinic-based dispersion were unsuccessful in effecting triaryl phosphine (TPP) reduction.

While not being bound by any particular theory, it is believed that a key to the invention is the balance (of redox potentials) between a polyaromatic hydrocarbon accepting an electron and then giving it up to a triaryl phosphine aryl group during the course of alkali metal diaryl phosphide salt formation. In effect the polyaromatic hydrocarbon serves a 1) a dissolution agent to generate favorable homogeneous reduction conditions, and 2) a catalyst that shuttles electrons between the alkali metal and the triaryl phosphine to give the desired alkali metal diaryl phosphide. Therefore, a more electron accepting aryl group, i.e. more electron deficient aryl group will possess a greater reactivity towards a given polyaromatic hydrocarbon radical anion. In effect increased selectivity and/or enhanced reactivity may be imparted by matching redox potentials between the alkali metal, the polyaromatic hydrocarbon, the intermediate alkali metal polyaromatic hydrocarbon radical anion, the triaryl phosphine, and the alkali metal diaryl phosphide.

Small Molecule Napthenics

A second form of useful PAH is that of a discrete small molecule such as naphthalene or its (per)alkylated analogs. Examples include, but are not limited to naphthalene, [1-methyl]naphthalene, [2-methyl]napthalene, [1,2-dimethyl] naphthalene, [1,6-dialkyl]naphthalene, anthracene, pyrene, polyaryls such as biphenyl, 4,4'-di(tert-butyl)biphenyl, 1-[N,N-dimethyl]naphthalene, etc. Several of these useful molecules are shown in Diagram 4. The small molecule naphthenics can be used at from 0.01-100 mol %, preferably from 0.1 to 10 mol %, and more preferably from 1 to 5 mol % of the naphthenic catalyst relative to the triaryl phosphine.

Diagram 4

1

2

3

Polymer Supported Naphthenics

A third form of the PAH are polymer supported polycyclic aromatic hydrocarbons. These would be the small molecule napthenics listed above that may be either pendant or main chain units, homopolymers or copolymers, without any regard to specific placement of one PAH catalytic unit to another. These could be formed by known synthetic processes. The copolymers could be random, blocky or gradient, and may be any known polymer architecture, including but not limited to, linear, comb, dendrimeric, star, or hyperbranched. Heteroatoms such as O, N, S may also be tolerated in either the polymer main chain or the pendant unit. By "copolymer" as used herein is meant a polymer consisting of two or more different monomeric units, including copolymers, terpolymers and other polymers having multiple different monomer units.

Typical incorporation of the PAH is from 1 mol % to 100 mol % (then a homopolymer). Specific to the copolymer would be a more desirable degree of naphthenic unit incorporation ranging from 1 mol % to 99 mol %, preferably from 5 to 75 mol %, and most preferably from 10 to 50 mol % naphthenic unit, Note that the limit of incorporation of the comonomer bearing the naphthenic catalyst unit is dictated more by the reactivity ratios of that naphthenic comonomer with the non-naphthenic, or diluent comonomer such as styrene. Typical Mns for the naphthenic catalyst-bearing homopolymer and the various copolymers would be from 500 to 1,000,000, preferably from 5,000 to 500,000, and more preferably from 10,000 to 100,000 g/mol. Diagrams 5 below shows useful napthenic homopolymers.

Diagram 5, Homopolymers:

P[1-VNap]

P[2-VNap]

P[4-1-NpCH$_2$CH$_2$OCH$_2$St]

P[x, y-dialkyl]naphthalene

Useful copolymers may be formed from ethylenically unsaturated monomer units, including, but are not limited to, polyamides, polyolefins, polyethers, polyamines, poly(meth) acrylates, polystyrenes. Sequential or simultaneous copolymerization or post-functionalization techniques may be used and should be evident by those skilled in the art. Diagram 6 shows exemplary copolymers, and Diagram 7 shows a useful method for a typical, but not limited to synthesis of napthenic-bearing vinyl monomers.

The copolymers may be prepared directly via copolymerization of a non-reactive diluent monomer such as styrene and a polymerizable precursor PAH such as [1-vinyl]naphthalene (See Diagrams 6-7), or by copolymerization via said means of a non-reactive diluent monomer such as styrene and a polymerizable monomer bearing a latent substituent that may be converted in a post-functionalization step to the polymer supported PAH such as [4-chloromethyl]styrene followed by benzylic chloride substitution with sodium [1-naphthyl] methoxide as shown in Diagrams 8, 9 and 10. Moreover, introduction of a light degree of cross-linking serves to facilitate recovery and/or separation of the polymer-supported naphthenic catalyst from the finished product, but does not tend to enhance any rate of triayl phosphine derivative reduction to the diaryl phosphide. Desirable ranges of divinyl benzene as cross-linking agent would be from 0.01 mol % to 5 mol %, but more desirable would be from 0.1 mol % to 2.5 mol %, and most desirable would be from 0.25-1 mol %.

Diagram 6, Random Copolymers:

PSt-co-P[4-[1-NpCH$_2$CH$_2$OCH$_2$]St x = 0.80
y = 0.20

PSt-co-P[4-[1-NpCH$_2$CH$_2$OCH$_2$]St-co-DVB x = 0.7975
y = 0.20
z = 0.0025

Diagram 7, Monomer Synthesis:

Pre-Functionalized Monomer Approach:

Diagram 8

Diagram 9 x = 0.7975
y = 0.20
z = 0.0025

Diagram 10, Post PAH Functionalization:

Diagram 11

The diagram below provides the structures to the materials described in Table 1.

Table 1 below gives the respective molecular weights for the random copolymers prepared via controlled radical polymerization as determined by GPC in THF. The subsequent headings of Wt % $C_{10}H_7$, mg Nap/1.0 g polymer and mmol Nap/1.0 g Polymer are calculations used to determine how much naphthenic copolymer should be added to a triarylphosphine reduction reaction. In other words, for a 5 mol % naphthenic charge to a 100 mmol phosphine reduction, 5 mmol of polymer supported naphthenic is needed, or roughly 0.90 g of P[1-Vnap].

TABLE 1

Calculation of Polymer Supported Naphthenic Catalyst Loading Levels.

| Naphthenic Polymer | Avg. Mol. Wt. (mg/mmol) | Wt % $C_{10}H_7$ | Mg Nap/ 1.0 g Polymer | mmol Nap/ 1.0 g Polymer |
|---|---|---|---|---|
| P[1-VNap] | 154.13 | 82.5 | 825.0 | 6.49 |
| P[2-VNap] | 154.13 | 82.5 | 825.0 | 6.49 |
| P[4-[1-naphthylCH$_2$CH$_2$OCH$_2$]] | 288.23 | 44.10 | 441.0 | 3.47 |
| PSt-co-P[4-[1-naphthylCH$_2$CH$_2$OCH$_2$]] | 140.92 | 18.0 | 180.0 | 1.42 |
| PSt-co-P[4-[1-naphthylCH$_2$CH$_2$OCH$_2$]]-co-[4-CMS] | 121.32 | 5.59 | 55.9 | 0.46 |
| PSt-co-P[4-[1-naphthylCH$_2$CH$_2$OCH$_2$]]-co-[1,4-DVB] | 140.99 | 25.42 | 254.2 | 2.00 |

Used the $C_{10}H_7$ unit at 127.11 mg/mmol as the basis for calculating the mmol Nap/1.0 g Polymer values.

Variations of the reduction reaction of a triaryl phosphine with the PAHs of the invention are also contemplated by the invention. In one embodiment, the phosphine derivatives may be added subsequent to the "pre-activation" of the PAH and sodium metal, i.e. formation of the PAH-alkali metal radical anion complex, or in a separate reactor, the PAH and the sodium metal may be "pre-activated" and then transferred to another reactor containing the full sodium and phosphine derivative complement. This "pre-activation" step appears to remove or suppress an induction period and noticeably enhances rates of reaction versus charging all components simultaneously with subsequent heating.

The aromatic radical anion catalyst may be eliminated or removed at either the intermediate diaryl phosphide step or the finished product mono-substituted diaryl phosphine, once either is sufficiently produced, using typical separation techniques known to those skilled in the art, such a filtration, vacuum strip or distillation, precipitation, or crystallization. Specific to perhydrotreated naphthenic oils, a 1-5 wt % aqueous acetonitrile-heptane phase split is used to partition the desired product to the acetonitrile phase and the oil to the iso-heptane phase. Separation of the perhydrotreated naphthenic oil from the crude mono-substituted diaryl phosphine products via these multiple aqueous acetonitrile phase splits leads to greater than 95% separation prior to crystallization of the diaryl phosphine product using a suitable solvent. In the absence of such phase splits and modified process steps, insufficient removal of the oil prior to crystallization either prevents any crystallization from occurring or significantly reduces product yield. The small molecule PAHs can be removed either via vacuum strip, chemical modification via reaction with carbon dioxide, or as a result of mono-substituted diaryl phosphine crystallization steps. Polymer supported radical anion catalysts are removed via simple nonsolvent precipitation.

The PAH electron transfer reduction catalysts of the invention may also be used for the formation of asymmetric or chiral phosphines, bis(phopshines), or poly(phosphines) from their respective prochiral phosphine precursors and their aforementioned derivatives via addition of an electrophile such as those described above, i.e. alkyl halides in the presence of a chiral co-catalyst that by interacting with the intermediate sodium diaryl phosphide salt renders the resulting product to be optically enriched in one enantiomer. Such enrichments are often the result of a preferential interaction between the chiral co-catalyst such as sparteine and the sodium diaryl phosphide followed by nucleophilic substitution of the electrophile in such a way that facial selectivity is imparted and an optically enriched product results.

The PAH reagents of the invention could also be used as easily removable or tailored polymer supported catalysts for alkyllithium reagent formation. Naphthalene has been reported to be a catalyst for the formation of n-butyllithium from lithium metal and n-butyl halides (See Holy, N. L. Chem. Rev. 1974, 74, 243 and Yus, M.; Herrera, R. P.; Guijarro, A. Tet. Lett. 2003, 44, 5025-5027 (R-F)).

The invention may be extended to derive optically active, P-chiral substituted diaryl phosphines whether the precursor triaryl phosphine derivative is achiral or chiral and whether the optical configuration of the mono-substituted diaryl phosphine results from the formation and/or transformation of the intermediate sodium diaryl phosphide salt. To derive such asymmetric derivatives, a chiral co-catalyst such as sparteine be added prior to coupling the sodium diaryl phosphide salt to an electrophile such as an alkyl halide.

EXAMPLES

All polymerizations, as described below were done under batch conditions, i.e. all reactants were charged to the reactor, it was heated to effect polymerization, the polymer was isolated via precipitation, dried, and then evaluated for its ability to reduce a given triaryl phosphine to the corresponding sodium diarylphosphide salt.

Carbon black was added as a dispersion stabilizer during triaryl phosphine reductions to prevent the adverse event of dispersed alkali metal agglomeration.

Experimental:

All solvents used were anhydrous unless otherwise stated. The living radical nitroxide initiator Blocbuilder® from Arkema Inc. All air sensitive and pyrophoric materials were handled using generally accepted inert atmosphere handling techniques. Sodium dispersions were prepared using an IKA LR 2000 laboratory reactor system consisting of either a jacketed 2 liter or 500 mL kettle with a bottom Teflon® stopcock drain, a central sweep agitator capable of up to 200-900 rpm, an internal temperature probe, and a self-contained, and a high speed dispersator (homogenizer) with a rotor-stator design capable of variable speeds between 8,000-24,000 rpm. Heating was provided by a Julabo oil bath and stainless steel flex hose and Teflon® snub connectors was used to connect the recirculating, heated bath oil to the reactor jacket. Both the heating and agitation were controlled by computer and a hydraulic lift stand was used to raise and lower the reactor from the head unit. The reactor was vented to an $N_2$ bubbler for inert atmosphere operation and setup in appropriate secondary containment in case of reactor breakage or oil leaks.

1). General Procedure for Sodium Dispersion Preparation: The general procedure for 33 wt % sodium dispersion preparation is as follows: The respective dispersion oil to be evaluated was weighed out and charged to the dry, nitrogen flushed reactor. The sodium (cubes in oil) was first washed in a beaker of mineral spirits and then transferred to a tared beaker of respective dispersion oil. The excess oil was decanted and the sodium cubes added directly to the same oil in the reactor. The oil in the oil bath was heated and then recirculated through the reactor jacket to the melting point of sodium. Once the internal temperature reached 99.7° C., the molten sodium was then broken up with the central, low rpm agitator consisting of a two prong turbine rotor over 10-15 minutes. Then the oil bath temperature was increased to 110-115° C. for an internal reactor temperature of 101-110° C. during dispersion formation. The reactor was cooled slightly form 115° C. to 102° C. as the sodium finished melting. Once at 102° C., the homogenizer was turned on for 30-60 minutes to disperse the sodium metal initially at 8000 rpm. The speed was then rapidly increased to 24,000 rpm and held for an additional 60-120 minutes. As the internal temperature approaches 109° C., the homogenizer speed is reduced to 8000 rpm, and then switched off. Once below 70° C., the dispersion was cooled below the melting point of sodium, the central agitator was restarted to remix or suspend the dispersion. At 45° C. or less the dispersion was then transferred using a vacuum transfer tube to a tared 500 mL receiver flask. The dispersion is then weighed and then poured into an argon purged HDPE wide mouth bottle for storage and tested within 48 hours to minimize adverse effects of settling. Particle sizes (by 20-40× microscope) should be measured within 24 hours of preparation.

2). Sodium Diarylphosphide Formation Via Reducing Alkali Metals:

2 A). Sodium Diarylphosphides Via Sodium Dispersions:

A 250 mL 3 neck round bottom flask equipped with a thermometer and its adapter, an overhead mechanical stirrer and its adapter through a reflux condenser, and a Claisen adapter to which is attached a 125 mL addition funnel with a rubber septum on top and a gas inlet. The entire apparatus is flushed with $N_2$ flow and heating for 30 minutes. After cooling the reactor is charged with 16.5 grams of 33 wt % Na dispersion (5.5 grams, 239.2 mmol Na) in perhydrotreated naphthenic oil and 600 gram of Acticarbone® carbon black (3.7 wt %). A separate 250 mL 1 neck round bottom flask is charged with 72.2 mmol of triarylphosphine, sealed with a rubber septum, and degassed with a rapid flow of $N_2$ for at least 30 minutes. The phosphine is then dissolved in 100 mL of anhydrous, degassed THF, transferred to the addition funnel via cannula, and added dropwise to the sodium dispersion with rapid mechanical agitation. The solution initially turns a yellow-green color and then the dark red color characteristic of sodium diarylphosphide salts. After roughly 50% of the phosphine solution is added, the reaction exothermed up to 45° C. (for triphenylphosphine). After all of the triaryl phosphine is added, the solution is held at 55° C. for 60 minutes or until $^{31}P$ NMR analyses indicate quantitative triphenyl phosphine reduction has occurred, cooled to room temperature, and either taken on directly to subsequent coupling steps or transferred to appropriate inert atmosphere storage equipment until further use. The reduction to the corresponding $Ph_2PNa$ salt is quantitative by $^{31}P$ NMR after 4-6 hrs. (THF: δ=−25.87 ppm).

2B). Small Molecule Naphthenic Catalyzed Sodium Diarylphosphide Formation:

2Bi). Solid Sodium Metal Route: A 50 mL 3 neck round bottom flask equipped with a thermometer and its adapter, a reflux condenser with a gas inlet atop, and a rubber septum secured with a ban of copper wire was charged with a Teflon® coated stir bar and 400 mg (17.4 mmol) of sodium metal cubes and 4.62 mmol) of the triarylphosphine. The sodium metal was cut from a large chunk in a beaker under pentane and heptane. The assembled apparatus was then flushed with a rapid flow of $N_2$ for 30 minutes. A 4 dram glass vial was charged with 0.25 mmol of the (1-methylnaphthalene additive and 10 mL of anhydrous THF. The 50 mL reactor was then charged with 15 mL of anhydrous THF and heated to 55° C. using an oil bath. After at least 30 minutes at 55° C., the naphthenic additive dissolved in THF was added all at once via cannula to the phosphine solution and the reactor continued heating overnight at 55° C. Alternatively, after degassing the charged phosphine and sodium, the degassed, anhydrous THF and the naphthenic catalyst may be added directly to the reactor followed by heating to 55° C. Samples were periodically withdrawn by syringe and placed in a degassed 5 mm NMR tube sealed with a rubber septum and a band of copper wire for analysis by $^{31}P$ NMR. In some cases excess BuBr (500 μL) was added via syringe to the NMR tube sample to verify product distribution observed by $^{31}P$ NMR for the crude sample removed from the reaction mixture, i.e. extent of sodium diarylphosphide formation (See below for various sodium diarylphosphide salts quantitatively prepared as described here). Reactions were typically quantitative within 16-48 hrs. depending on the amount of naphthenic catalyst charged and the electron-rich nature of the triaryl phosphine being reduced to its sodium diarylphosphide salt. GC/MS can also be used to verify percent conversion by reacting the intermediate sodium diarylphosphide salt with a slight excess of butyl bromide, conducting an aqueous phase split between toluene and water, drying the organic phase over anhydrous magnesium sulfate, and then injecting via syringe onto the GC column. GC and $^{31}P$ NMR measurements agreed with each other within 1-2%.

Various triaryl phosphines successfully reduced as described conditions in B). i). above.

Sodium (2-tolyl)$_2$PNa in THF: δ=−41.49 ppm.
Sodium (4-tolyl)$_2$PNa in THF: δ=−29.64 ppm
Sodium (3,5-xylyl)$_2$PNa in THF: δ=−25.95 ppm 2Bii). Solid Alkali Metal Mixture Route: A 250 mL 3-neck glass resin kettle equipped with a thermometer and its adapter, and overhead mechanical stirrer assembly, and a Claisen adapter to which is attached a reflux condenser with a gas inlet on top and a Teflon® stopcock sample port is heated with a heat gun to 75° C. while flushing with a rapid $N_2$ purge for 1 hr. Then a solid piece of sodium (5.0 grams, 217.5 mmol) and potassium (500 mg, 12.8 mmol) are added, the reactor resealed and flushed with $N_2$ for an additional 30 minutes. Then 60 mL of anhydrous toluene is added and the reactor assembly immersed in a thermostated oil bath and heated to 115-118° C. to melt the sodium and potassium. After rapidly stirring the molten alkali metal mixture for 30-60 minutes, the heat is removed, the stirring ceased, and the contents allowed to settle while slowly cooling to 25° C. The toluene is then removed by decanting through a cannula.

In a dry box, a separate 250 mL 1 neck round glass bottom flask is loaded with 25 grains of tris(3,4-xylyl)phosphine (72.2 mmol, 3,4-TXP), the flask sealed with a rubber septum secured by a copper wire band. In the hood, the phosphine in the 250 mL flask is briefly degassed for 30 minutes and then 100 mL of degassed THF and 250-500 μL (1.8-3.5 mmol, 2.5-5.0 mol %) of (1-methyl)naphthalene catalyst are added by calibrated syringe. After gently shaking the flask to effect complete 3,4-TXP dissolution, the phosphine solution is transferred via cannula through the sample port to the alkali metal reactor. Once the transfer of the 3,4-TXP-catalyst solution is complete, the reactor is reimmersed in the thermostated oil bath and heated to 55° C. The conversion of the 3,4-TXP to the corresponding sodium bis(3,4-xylyl)phosphine (72.2 mmol, 3,4-BXPNa) by $^{31}$P NMR. In order to follow the conversion, solution samples are periodically withdrawn by either syringe or cannula and transferred to an $N_2$ inerted 5 mm NMR tube sealed with a rubber septum. The reduction to the corresponding bis(3,4-xylyl)PNa salt is quantitative by $^{31}$P NMR after 20 hrs. (THF: δ=−30.50 ppm).

2C). Preparation of Sodium Diarylphosphide Via Polymer-Supported Naphthenic Catalysts:

2Ci). A 50 mL 3 neck round bottom flask equipped with a thermometer and its adapter, a reflux condenser with a gas inlet atop, and a rubber septum secured with a ban of copper wire was charged with a Teflon® coated stir bar. The reactor assembly was then heated to 85-90° C. with a heat gun and purged with a rapid flow of $N_2$ or 30-45 minutes. Then 400 mg (17.4 mmol) of sodium metal cubes and 1.6 g (4.62 mmol) of the tris[3,5-xylyl]phosphine, [3,5-TXP], and enough polymer supported naphthenic catalyst [6.49-1.42 mmol/1000 mg of (co)polymer See calculation below and Tables 2-4 for actual charges] to give 3.8 mol % naphthalene (as $C_{10}H_7$) relative to the phosphine were charged. The sodium metal was cut from a large chunk in a beaker under pentane and weighed in a tared, sealed 4 dram glass vial containing heptane. The reactor assembly was then purged for an additional 15-20 minutes with a rapid $N_2$ flow at 25° C. Then the 50 mL reactor was charged with 25 mL of anhydrous THF by syringe followed by overnight heating at 55° C. using an oil bath. Samples were periodically withdrawn by syringe and placed in a degassed 5 mm NMR tube sealed with a rubber septum and a band of copper wire for analysis by $^{31}$P NMR. Prior to aliquot addition, the sealed tube was likewise heated to 75-80° C. with a rapid $N_2$ purge for 15-30 minutes. In some cases excess BuBr (500 μL) was added via syringe to the NMR tube sample to verify product distribution and selectivity as observed by $^{31}$P NMR for the crude sample removed from the reaction mixture, i.e. whether any diphenylphosphole or other by-products formed.

Calculation of Naphthalene Fragment $C_{10}H_7$ mmol/1.0 gram of (Co)Polymer:

$$\frac{[C_{10}H_7][\text{mol\% naphthenic}]}{\text{Monomer average MW}} = \frac{[127.11 \text{ mg}][\text{mol\% naphthenic}]}{\text{Monomer average MW}}$$

A. $P[1 - VNp]$: $\frac{C_{10}H_7}{C_{12}H_{10}} = \frac{[127.11 \text{ mg}][100 \text{mol\% naphthenic}]}{[154.13 \text{ mg}]} =$ 82.5 wt% $C_{10}H_7$ Therefore: $\frac{[825 \text{ mg } C_{10}H_7]}{[1000 \text{ mg (co)polymer}][127.11 \text{ mg/mmol}]} =$ $\frac{6.49 \text{ mmol } C_{10}H_7}{1000 \text{ mg (co)polymer}}$ A. Small Molecule Co-Catalyst Addition:

If (1-methyl)naphthalene was added as a co-catalyst, a 4 dram glass vial was charged with 110 mg of the naphthenic additive to which was added 10 mL of anhydrous THF to give a solution that was 0.0775M naphthenic in THF. An appropriate amount of the co-catalyst was then added directly to the reactor using a gas-tight, microliter syringe followed by continued heating of the reactor overnight at 55° C.

3). Polymer Supported Naphthenic Catalyst Formation:
3A). Post-Functionalization Approach:
3Ai). Controlled Radical Polymerization of Styrene and (4-Chloromethyl)Styrene:

A 3 neck, 1 liter reactor equipped with a thermometer and its adapter, and overhead mechanical stirrer and its adapter, and a Claisen adapter to which was attached a rubber septum and a reflux condenser with an $N_2$ inlet atop was flushed with a rapid flow of $N_2$ for 30 minutes while heating with a heat gun. Then 1.5 grams of Blocbuilder® initiator was added and the reactor $N_2$ purged for an additional 30 minutes, followed by 250 mL of anhydrous, degassed toluene via cannula. In a separate 250 mL 1 neck round bottom degassed flask sealed with a rubber septum was added styrene (91.5 grams, 806.3 mmol, 3 eq.) and (4-chloromethyl)styrene or (4-CMS) (33.5 grams, 268.8 mmol, 1 eq.). The 3:1 monomer mixture was gently $N_2$ sparged for 15 minutes to degas and then transferred via cannula to the toluene solution. A heating mantle was placed beneath the reactor assembly and the contents heated to 100-110° C. overnight to effect copolymerization. After cooling the contents to 25° C., the polymerization mixture was diluted with 100 mL of MeOH, stirred to completely mix, and then added dropwise to a 10-fold excess of rapidly stirred MeOH to precipitate the random copolymer. The precipitated copolymer was isolated using suction filtration through a glass fritted funnel, rinsed with 3×100 mL of fresh MeOH, and then transferred to a 500 mL beaker, and dried in a vacuum oven at 60° C. overnight. The 90.2 grams of random copolymer was isolated in 72% yield as a fluffy white solid of low bulk density. The random copolymer was then dissolved in CDCl$_3$ and characterized by $^1$H(CDCl$_3$: δ=7.40-6.15 ppm, cm, 9H, aromatic, 58.15 area %; δ=4.435-4.302 ppm, broad doublet, 2H, —CH$_2$Cl, 5 area %; S=1.961-1.012 ppm, cm, 3H, —CH$_2$—CH-36.85 area %). Theoretical benzylic area % for random copolymer is 6.1 area % compared to 5.0 area % experimental via 1H NMR. Therefore the ratio of styrene:4-CMS is 3.6:1 or roughly 4:1 in the isolated random copolymer (See Table X above). $^{13}$C NMR also supports the random copolymer structure. GPC analysis in THF gives molecular weight properties of M$_n$=428.2, PDI=1.60.

3Aii). Naphthenic Unit Conjugation—Preparation of 4-[(1-naphthyl)CH$_2$OCH$_2$]styrene:

A 500 mL 3 neck round-bottomed flask was equipped with a thermometer and its adapter, an overhead mechanical stirrer and its adapter, and a Claisen adapter to which was attached a 60 mL addition funnel with a rubber septum on top and a gas inlet. The reactor assembly was heated to 80-85° C. with a heat gun while purging with a rapid flow of $N_2$ followed by an additional 30 minutes of $N_2$ flow while cooling back to 25° C. Once cooled to 25° C., sodium hydride (NaH as a 60 wt % dispersion in mineral oil, 0.97 grams, 40 mmol) was charged to the reactor. A separate 100 mL 1 neck round-bottomed flask was then charged with 6.32 grams (40 mmol) of (1-naphthyl)methanol and 35 mL of anhydrous THF. The NaH was then suspended in 25 mL of THF and the alcohol solution transferred by cannula to the addition funnel in parts and added dropwise over 30 minutes to the NaH suspension. No rapid off-gassing was observed during the alcohol addition. A heating mantle was placed beneath the reactor and its contents heated to 35° C. overnight for 16 hrs. A separate 250 mL 1 neck round bottom flask was charged with 30 grams of the random styrene-co-4-CMS copolymer, sealed with a rubber septum, and then degassed for 2 hours with a rapid flow of N$_2$. Then the polymer was dissolved in 250 mL of anhydrous THF and transferred via cannula to the 500 mL reactor containing the naphthylethoxide salt. A heating mantle was placed beneath the reactor and its contents heated for 16 hours at 50-55° C. After cooling the reactor to 25° C., the solution was transferred to a 1 L 1 neck flask and the solvent reduced by thirty percent with the use of a rotary evaporator. Then the polymer solution was precipitated into a 10-fold excess of rapidly stirring hexanes ensuring fine polymer particles formed. The solids were recovered on a coarse fritted funnel using suction filtration, collected in a beaker and then placed in a vacuum oven overnight at 60° C. to dry. $^1$H NMR analysis showed only 31% benzylic chloride substitution to give the desired (1-naphthyl)methoxide pendant unit giving roughly 0.42 mmol "naphthenic" per 1 gram of polymer. The random terpolymer was then used as is in the evaluation of triaryl phosphine reductions. GPC analysis in THF gives molecular weight properties of $M_n$=405.1, PDI=1.65.

3B). Pre-Functionalized Monomer Approach:

3Bi). Preparation of 4-[(1-naphthyl)CH$_2$CH$_2$OCH$_2$]styrene (11)

A 250 mL 3 neck round-bottomed flask was equipped with a thermometer and its adapter, an overhead mechanical stirrer and its adapter, and a Claisen adapter to which was attached a 60 mL addition funnel with a rubber septum on top and a gas inlet. The reactor assembly was heated to 80-85° C. with a heat gun while purging with a rapid flow of N$_2$ followed by an additional 30 minutes of N$_2$ flow while cooling back to 25° C. Once cooled to 25° C., sodium hydride (NaH as a 60 wt % dispersion in mineral oil, 4.2 grams, 174 mmol) was charged to the reactor. A separate 250 mL 1 neck round-bottomed flask was then charged with 25 grams (145.2 mmol) of 2-(1-naphthyl)ethanol and 125 mL of anhydrous THF. The NaH was then suspended in 25 mL of THF and the alcohol solution transferred by cannula to the addition funnel in parts and added dropwise over 30 minutes to the NaH suspension. No rapid off-gassing was observed during the alcohol addition, A heating mantle was placed beneath the reactor and its contents heated to 35° C. overnight for 16 hrs. A second 100 mL 1 neck round-bottomed flask was charged with 22.2 grams (145.2 mmol) of (4-chloromethyl)styrene and 40 mL of anhydrous THF, mechanically agitated to mix, and then transferred by cannula to the addition funnel and added dropwise to the sodium alkoxide suspension in THF. No exotherm was observed. A heating mantle was placed beneath the reactor and the contents heated to 55° C. for 1 hour with mechanical agitation. A small aliquot of the crude product suspension was removed by syringe, subjected to and aqueous workup, and then analyzed by GC/MS. The desired product was observed, therefore the heating mantle was removed, the suspension cooled to 25° C., and the volatiles removed using a rotary evaporator. The viscous solid was then partitioned between 250 mL deionized H$_2$O and 200 mL of reagent grade methylene chloride. After a phase split, the organic phase was washed with 1×150 mL of 0.1M aq. HCl, 1×100 mL of deionized H$_2$O, 1×150 mL of saturated aq. NaHCO$_3$, 1×100 mL of brine solution, and then dried over anhydrous MgSO$_4$. After 1 hour, all insolubles were removed via gravity filtration using filter paper and the volatiles again removed using a rotary evaporator. The product was analyzed by NMR and GC/MS, diluted to give a 25 wt % naphthenic monomer in toluene (d=0.886 g/mL), and then stored in a refrigerator until (co)polymerized as described below. GC/MS experimental: m/z=288; theoretical m/z=288.23. Both the $^1$H NMR and the $^{13}$C NMR analyses using a 300 MHz NMR in CDCl$_3$ showed splitting patterns and chemical shifts consistent with the desired monomer product.

3Bii). Controlled radical Polymerization (CRP) of 4-[1-naphthylCH$_2$CH$_2$OCH$_2$]styrene and its Styrene Copolymers (1-3)

A thermometer and its adapter, an overhead mechanical stirrer and its adapter, and a Claisen adapter to which was attached a reflux condenser with a gas inlet on top and a 60-125 mL addition funnel with a rubber septum secured with a band of copper wire were attached to a 250 mL 3-neck round-bottomed flask. The reactor assembly was heated with a heat gun to 75-80° C. and flushed with a rapid flow of N$_2$ for at least 30 minutes while cooling to 25° C. Then 40 mL of degassed toluene, 10 mL (9.09 g) of styrene, and 36 mL (31.9 g) of a 8 grams of styryl(naphthylethanoxy) monomer (11) as a 25 wt % solution in toluene (d=0.886 g/mL) were introduced by syringe. The comonomer solution was degassed with a secondary rapid flow of N$_2$ introduced by a needle for at least 15 minutes. In a separate 25 mL one neck round-bottomed flask sealed 140 mg of BLOCBUILDER alkoxyamine initiator (350 mg/mmol) was placed. The flask was sealed with a rubber septum and a band of copper wire, flushed with a rapid flow of N$_2$ for 15 minutes at 25° C., then added 10 mL of degassed toluene by syringe. The solution was further degassed for another 5 minutes (toluene degassed in a prior step) and then transferred all at once to the polymerization reactor by cannula. The monomer-initiator solution was then heated to 105-110° C. for at least 18 hrs. under an N$_2$ atmosphere to effect copolymerization. The reaction mixture was then cooled to 25° C. from which approximately 50% of the volatiles were removed using a rotary evaporator to concentrate the copolymer. The copolymer was then precipitated into a 12-fold excess of heptane. The precipitated solids were isolated via vacuum filtration using a glass-fritted funnel and then dried in a vacuum oven at 10 mm Hg and 65° C. for 72 hrs. The dried copolymer was then characterized by $^1$H and $^{13}$C NMR as a concentrated solution in CDCl$_3$ and showed splitting patterns and chemical shift values consistent with the desired copolymer structure. Again, the copolymer was roughly 20 mol % of the styryl(1-naphthylethoxy) repeat unit and 80 mol % styrene.

3Biii). Emulsion (Co)Polymerization of (2-Vinyl)naphthalene and Styrene

A thermometer and its adapter, an overhead mechanical stirrer and its adapter, and a Claisen adapter to which was attached a reflux condenser with a gas inlet on top and a 60-125 mL addition funnel with a rubber septum secured with a band of copper wire were attached to a 1000 mL 4-neck round-bottomed flask. The reactor assembly was heated with a heat gun to 75-80° C. and flushed with a rapid flow of N$_2$ for at least 30 minutes while cooling to 25° C. In four separate 4-dram glass vials were placed 5.84 g (16.8 mmol) of SDBS surfactant, 420 mg (2.21 mmol) of Na$_2$S$_2$O$_5$, 420 mg ((5.03 mmol) of NaHCO$_3$, and 600 mg (2.21 mmol) of K$_2$S$_2$O$_8$ initiator. The Na$_2$S$_2$O$_5$, NaHCO$_3$, and the K$_2$S$_2$O$_8$ solids were dissolved in 10 mL of degassed H$_2$O, respectively followed by degassing with a gentle N$_2$ purge for 10 minutes. Note, the former two readily dissolved, while the latter K$_2$S$_2$O$_8$ require significantly more time to dissolve. The reactor assembly was then charged with 300 mL of deionized water and the 5.84 g (16.8 mmol) of SDBS surfactant followed by degassing with a rapid sparge of N$_2$ by introducing a needle through the rubber septum. In a separate 100 mL 1-neck flask was placed 41.3 g (397 mmol) of styrene and 6.8 g of (2-vinyl)naphthalene (44.10 mmol) that were mixed with a gentle N$_2$ purge for 5 minutes.

A heating mantle was placed beneath the polymerization reactor and the water phase heated to 50° C. The monomer solutions was then added by cannula, followed by the NaHCO$_3$ solution, the Na$_2$S$_2$O$_5$ solution, and finally the K$_2$S$_2$O$_8$ solution. The last K$_2$S$_2$O$_8$ was added dropwise from the addition funnel to modulate the copolymerization exotherm. A slight 5° C. exotherm was observed. After 1.5 hours an additional 170 mg of K$_2$S$_2$O$_8$ in 10 ml, of degassed water was added via syringe. The polymerization vessel was then heated overnight at 50-55° C. for 18 hrs. at which time the heating mantle was removed and the reactor cooled to 25° C. The copolymer was precipitated by dropwise addition into a methanolic solution containing CaCl$_2$ (4 grams in 250 mL MeOH).

Approximately 150 mL of deionized water was added to aid in precipitation. Note: not all of the copolymer was isolated, only enough (10 grams) to characterize and evaluate in the Na metal reduction of 3,5-TXP. Thermal analysis showed the suspension to be roughly 9.59 wt % solids (theory=9.34 wt % solids). The polymer precipitated immediately, was collected on a glass-fritted vacuum filtration funnel, rinsed with 10 mL of chilled MeOH, and then dried in a vacuum oven at 2 min Hg for 72 hrs.

4). General Sodium Diarylphosphide Salt Coupling Procedure:

4A). Sodium Diarylphosphides Prepared Via Sodium Dispersions—Method 2). A).

4Ai). Preparation of (−)-2,3-O-Isopropylidene-2,3-dihydroxy-1,4-bis(diphenyl phosphino)butane (−)-DIOP ligand: A 250 mL 3 neck round bottom glass reactor equipped with a Teflon® coated stir bar, a thermometer and its adapter, a reflux condenser with a gas inlet on top, and a Claisen adapter to which is attached a 60 mL addition funnel and a Teflon® stopcock sample port is heated with a heat gun while purging with a rapid flow of N$_2$ to degas. The reactor is then charged with 16.0 grams of (−)-1,4-di-O-tosyl-2,3-O-isopropylidene-L-threitol (CAS#37002-45-2, 36.1 mmol), aka bis(tosylate) and flushed with N$_2$ purge for an additional 30 minutes. The bis(tosylate) is then dissolved in 100 mL of degassed, anhydrous THF. The sodium diarylphosphide solution prepared in Step 2). A). above is then transferred via cannula to the 60 mL addition funnel in parts and added dropwise to the rapidly stirring bis(tosylate) at rate so as to maintain a reactor temperature below 40° C. Upon addition to the electrophile, the reddish-orange color of the diarylphosphide salt rapidly disappears to give a final suspension with a beige color. After all of the phosphide is added, an oil bath is placed beneath the reactor and the contents heated to 50° C. for 45 minutes to complete phosphide coupling step. The Claisen adapter assembly is then replaced by a short path distillation head and roughly 50% of the THF is removed. Then 100 mL of degassed heptane and water, each, are added to effect a phase split. The biphasic solution is then passed through an inerted glass fritted funnel to remove the carbon black and the lower aqueous phase removed via cannula. The upper organic phase is rinsed with an additional 50 mL of degassed water, again removed via cannula. The organic heptane phase is then extracted with 100 mL of anhydrous, degassed acetonitrile, the lower acetonitrile phase removed via cannula, and again the organic heptane phase is extracted with 50 mL of degassed acetonitrile. The acetonitrile phases are combined and transferred to a 1 neck round bottom flask with a Teflon® stopcock on top with a 24/40 standard tapered ground glass joint on top. The volatiles are removed on a rotary evaporator to yield a viscous orange-brown glassy solid that is further dried under vacuum. In a dry box, the Teflon® stopcock is replaced with a Claisen adapter to which is attached a reflux condenser with a gas inlet on top and a Teflon® stopcock sample port. The glassy solid is then dissolved in crystallized in 100 mL of degassed methanol introduced by cannula or syringe followed by heating to reflux to completely dissolve the ligand. The heat is removed and the DIOP ligand suspension in the flask is immersed in an ice batch and cooled to −10° C. to yield a white to off-white/beige colored solid. The solid DIOP ligand is collected on a glass fritted Schlenck filter, rinsed with chilled methanol, and then dried overnight on the frit under vacuum. A total of 11.7 grams (23.5 mmol, 498.34 g/moll) of the (−)-DIOP ligand was isolated. The ligand is fully characterized by $^1$H(CDCl$_3$: δ=7.58-7.29 ppm, cm, 20H, aromatic; δ=4.0-3.8 ppm, dd, 2H, —CH—; 6-2.50-2.25 ppm, ddd, 4H, —CH$_2$—; δ1.35 ppm, s, 6H, —CH$_3$) $^{13}$C (not reported here, but consistent with desired product), and $^{31}$P NMR (CDCl$_3$: δ=−22.87 ppm, singlet, and a mol % P purity>99%) and by ICP for a total phosphorus content of 12.2 wt % P (theory=12.4 wt % P) representing a chemical purity of approximately 98.4% for molecular formula=C$_{31}$H$_{32}$P$_2$O$_2$ and molecular weight=498.34 g/mol.

4B). Sodium Diarylphosphides Prepared Via Naphthelide Catalysis—Methods 2). B).-C).

4Bi). Preparation of (−)-2,3-O-Isopropylidene-2,3-dihydroxy-1,4-bis(3,5-dixylyl phosphino)butane (−)-3,5-BXP-DIOP ligand (CAS#220196-34-9): A 250 mL 3 neck round bottom glass reactor equipped with a Teflon® coated stir bar, a thermometer and its adapter, a reflux condenser with a gas inlet on top, and a Claisen adapter to which is attached a 60 mL addition funnel and a Teflon® stopcock sample port is heated with a heat gun while purging with a rapid flow of N$_2$ to degas. The reactor is then charged with 10.4 grams of (−)-1,4-dibromo-2,3-O-isopropylidene-L-threitol (CAS#73744-64-6, 36.1 mmol), aka dimethylketal-L-1,4-dibromide or dibromide and flushed with N$_2$ purge for an additional 30 minutes. The dibromide is then dissolved in 50 mL of degassed, anhydrous THF. The sodium diarylphosphide solution prepared in Step 2). B)-C). above is then transferred via cannula to the 60 mL addition funnel in parts and added dropwise to the rapidly stirring dibromide solution at rate so as to maintain a reactor temperature below 40° C. The reddish-orange color of the diarylphosphide salt rapidly disappears to give a final suspension with a beige color. After all of the phosphide is added, an oil bath is placed beneath the reactor and the contents heated to 40° C. for 45 minutes to complete phosphide coupling step. The Claisen adapter assembly is replaced by a short path distillation head, 5 mL of degassed iso-propanol is added to consume excess sodium and phosphide anion, and then roughly 50% of the THF is removed. Then 100 mL each of degassed toluene and water are added to effect a phase split. After rapid mixing, the phases are allowed to settle and the lower aqueous phase removed via cannula. The upper organic phase is rinsed with an additional 2×50 mL of degassed water, again removed via cannula. A Teflon® stopcock valve assembly with a 24/40 standard tapered ground glass joint is affixed to the top of the flask and the toluene volatiles removed on a rotary evaporator or other vacuum to yield a viscous orange-brown glassy solid that is further dried under high vacuum overnight. Care should be taken to maintain stringent air-free conditions. In a dry box, the Teflon® stopcock is replaced with a Claisen adapter to which is attached a reflux condenser with a gas inlet on top and a Teflon® stopcock sample port. The glassy solid is then dissolved in crystallized in 100 mL of degassed methanol introduced by cannula or syringe followed by heating to reflux to completely dissolve the ligand. The heat is removed and the 3,5-BXPDIOP ligand flask is immersed in an ice batch and cooled to <−10° C. to yield a white to off-white/beige colored, low melting point solid. The mother liquor is decanted via cannula away from the solidified (−)-3,5BXP-DIOP ligand, rinsed once with 25-30 mL of degassed methanol again cooled to <−10° C. and removed via cannula. The low melting point solid is then placed under high vacuum for further drying. A total of 16.5 grams (27.1 mmol, 610.43 g/mol) of 3,5-BXPDIOP is isolated. The ligand is fully characterized by $^1$H(CDCl$_3$: δ=7.15-6.85 ppm, cm, 12H, aromatic; δ=3.90-3.75 ppm, cm, 2H, —CH—; δ=2.45-2.20 ppm, cm, 4H, —CH$_2$—; δ=2.25 ppm, s, 24H, —CH$_3$; δ=1.35 ppm, s, 6H, —CH$_3$), $^{13}$C(CDCl$_3$: δ=137.86 ppm and 130.55 ppm, —CH— aromatic; δ=128.02 ppm and 125.95 ppm, 4°=CX— (for X=P or C), aromatic; δ=108.86 ppm, 4° C., ketal; δ=79.93 ppm, 3°=CH—; δ=32.49 ppm, 2°—CH$_2$—; δ=27.45 ppm, —CH$_3$, ketal; δ=21.47 ppm, —CH$_3$, aromatic), and $^{31}$P NMR (CDCl$_3$: δ=−26.98 ppm, singlet, and a mol % P purity>98%) and by ICP for a total phosphorus content of 10.0 wt % P (theory=10.2 wt % P) representing a chemical purity of approximately 98.5% for molecular formula=C$_{39}$H$_{48}$P$_2$O$_2$ and molecular weight=610.43 g/mol.

TABLE 2

Perhydrotreated Naphthenic Oils used in Na Dispersions for Alkali Metal Diaryl Phosphide Formation.

| Oil | Supplier | CAS# | % CAS# | Density | Visc. [40° C.] cSt | Aniline pt. ° F. | FP COC ° F. | Particle size microns | Mass Balance % Isolated |
|---|---|---|---|---|---|---|---|---|---|
| Standard: | | | | | | | | | |
| Shellflex 6212 | Shell | 64742-53-6 | 100 | 0.910 | 20-24 | 178 | 335 | 2-30 | 95.2 |
| Other:: | | | | | | | | | |
| Carnea E-22 | Shell | 64742-53-6 64742-52-5 | 35-50 50-65 | 0.887 | 21 | 178 | 335 | 1-10 | 93.8 |
| Carnea E-32 | Shell | 64742-53-6 64742-52-5 | 5-20 80-95 | 0.904 | 31 | 181 | 360 | 1-7 | 83.5 |
| Hyvolt II | Ergon | 64742-53-6 128-37-0 | >99.7 <0.3 | 0.889 | 9.6 | 158.7 | 306 | 2-5 | 97.9 |
| Hyprene 100 | Ergon | 64742-52-5 | 100 | 0.908 | 108 | 164 | 345 | 1-15 | 96.0 |
| Renoil 100S | Renkert | 64742-53-6 | 100 | 0.91 | 19.5 | 74 | 327 | 0.5-20 | 93.5 |
| Renoil 100HT | Renkert | 64742-53-6 64742-52-5 | Variable | 0.9071 | 20 | 73 | 331 | 2-20 | 89.5 |
| Nytro 10GBN | Nynas | 64742-53-6 | 100 | 0.890 | 9.1 | 69 | 302 | 2-7 | 98.8 |
| THN | Aldrich | 119-64-2 | 100 | 0.973 | NE | NE | 167 | 0.5-2 | 94.7 |
| THN in Xylene | Aldrich | 119-64-2 1330-20-7 | 50 50 | 0.913 | NE | NE | NE | 0.5-5 | 98.5 |

TABLE 3

Evaluation of TPP Reduction by Na Dispersions Prepared from Candidate oils from Table 1.
Method 2A was used to conduct the evaluations with screening of performance according to the values in Table 3. Specifically, incomplete reduction, low reactivity, and dispersed sodium agglomeration (Table 3), and impure and/or low product yield (Table 4) are all bad and therefore render a candidate oil/dispersion unacceptabkle as a Shellflex 6212 replacement.

| | | | Preparation | | | | Evaluation: TPP Reduction to Phosphide | | | | |
|---|---|---|---|---|---|---|---|---|---|---|---|
| Base Oils | Supplier | Color | Particle Size, microns | % Yield | Comments Agglomeration | ΔT ° C. (max.) | time $t_{\Delta T}$ (min.) @ ΔT max | % Conv. @ $^{60}t_m$ | % Conv. @ $^{240}t_m$ | % Phosphole | Comments Agglomeration |
| Standard: | | | | | | | | | | | |
| Shellflex 6212 | Shell | Light yellow. | 2-30 | 95.2 | | 13.344 | 16.381 | 72.99% | 82.24 | 4.40% | Yes. |
| Candidate: | | | | | | | | | | | |
| Carnea E-22 | Shell | Yellow-gold. | 1-10 | 93.8 | Some. | 12.283 | 14.344 | 80.76 | 87.06 | 1.69% | Slight. |
| Carnea E-32 | Shell | Gold. | 1-7 | 83.5 | Yes. | 12.953 | 13.010 | 82.55 | 84.29 | 1.61% | Yes. |
| Hyvolt II | Ergon | White. | 2-5 | 97.9 | Good yield. | 12.652 | 15.677 | 84.11 | 87.99 | 1.99% | No. |
| Hyprene | Ergon | Yellow. | 1-15 | 96.0 | Some. | 13.817 | 14.678 | 77.89 | 83.15 | 2.36% | No. |
| Renoil 100S | Renkert | Brown. | 0.5-20 | 93.5 | No. | 14.035 | 10.342 | 87.17 | 90.86 | 1.14% | Slight. |
| Renoil 100HT | Renkert | Brown-purple. | 2-20 | 89.5 | Some. | 13.762 | 13.001 | 71.33 | 67.16 | 0.74% | Severe. |

TABLE 3-continued

Evaluation of TPP Reduction by Na Dispersions Prepared from Candidate oils from Table 1.
Method 2A was used to conduct the evaluations with screening of performance according to the values in Table 3. Specifically,
incomplete reduction, low reactivity, and dispersed sodium agglomeration (Table 3), and impure and/or low product yield (Table 4)
are all bad and therefore render a candidate oil/dispersion unacceptabkle as a Shellflex 6212 replacement.

| Base Oils | Supplier | Color | Preparation | | | Evaluation: TPP Reduction to Phosphide | | | | | |
|---|---|---|---|---|---|---|---|---|---|---|---|
| | | | Particle Size, microns | % Yield | Comments Agglomeration | $\Delta T$ °C. (max.) | time $t_{\Delta T}$ (min.) @ $\Delta T$ max | % Conv. @ $^{60}t_m$ | % Conv. @ $^{240}t_m$ | % Phosphole | Comments Agglomeration |
| Nytro 10GBN | Nynas | White. | 2-7 | 98.8 | Thin oil. No. | 12.673 | 18.014 | 72.70 | 64.26 | 2.36% | Slight. |
| THN | Aldrich | Light yellow. | 0.5-2 | 94.7 | No. | 13.312 | 7.673 | 79.93 | 89.08 | 0.47% | No. |
| THN in Xylene | Aldrich | Yellow-brown. | 0.5-5 | 98.5. | No. | 10.476 | 26.021 | 79.53 | 97.71 | 1.10% | No. |

Note:
Results of screening various perhydrotreated naphthenic oils and their corresponding 33 wt % sodium dispersion in their efficiency of reducing triphenyl phosphine (TPP) to the sodium diaryl phosphide salt product.
a. $\Delta T$ °C. = Value of maximum exotherm observed upon charging TPP to Na dispersion.
b. Time $t_m$ (min.) = Time to reach maximum exotherm after charging TPP to Na dispersion.
c. % Conv. @ $^{60}t_m$ = The % TPP conversion to the diphenyl phosphide anion 60 minutes after the onset of TPP addition to the Na dispersion.
d. % Conv. @ $^{240}t_m$ = The % TPP conversion to the diphenyl phosphide anion 240 minutes after the onset of TPP addition to the Na dispersion.

TABLE 4

Evaluation of Sodium Dispersions in Various Candidate Oils via DIOP Ligand Synthesis.

| Run # | Dispersion | Prepared by | DIOP Recovery | | | | Wt % LOD | | DIOP Appearance |
|---|---|---|---|---|---|---|---|---|---|
| | | | Crude | | Crystallized | | Heptane Phase | MeOH Phase | |
| | | | Wt (g) | % Yield | Wt (g) | % Yield | | | |
| 1 | Hyvolt II | Supplier | 17.0 | 85% | 10.82 | 54.1% | 7.4% | 9.6% | Fluffy, light yellow. |
| 2 | Hyvolt II | Arkema-KoP | 15.0 | 75% | 9.40 | 47.0% | — | 7.4% | Chunky, light yellow. |
| 3 | Renoil 100S | Arkema-KoP | 15.1 | 75% | 6.71 | 33.6% | 8.8% | 8.0% | Powder, light beige. |
| 4 | Carnea E-22 | Arkema-KoP | 18.0 | 90% | 12.14 | 60.7% | 10.0% | 7.8% | Granular, manilla. |
| 5 | Nynas 10 GBN | Arkema-KoP | 16.1 | 81% | 10.15 | 50.8% | 11.6% | 9.6% | Granular, off-white. |
| 6 | THN in Xylenes | Arkema-KoP | 15.0 | 75% | 7.43 | 37.2% | 4.8% | 9.0% | Chunky, light yellow. |

Example 2:
See Method 2). B). i). For general method of conducting these naphthenic catalyst evaluations. $^{31}$P NMR was sued to screen the rate of and selectivity for the desired sodium diphenyl phosphide salt. In all cases with TPP, a known phosphole by-product forms that does not form when the sodium dispersions are used in the reduction of TPP.

TABLE 5

Na-Naphthalene Reduction of TPP to Sodium Diphenyl Phosphide.

| Expt. | Additive Identity | Conditions | | | | Results | | |
|---|---|---|---|---|---|---|---|---|
| 5a | | Mol % | Temp. ° C. | BHT | Time (hrs.) | % Conversion | Mol % Ph$_2$PNa | Mol % Phosphole |
| 5b | Anthracene | 5.0 | 45 | None | 18.0 | 69.84 | 57.49 | 8.79 |
| 5c | Phenanthrene | | | | 18.0 | 100.0 | 90.97 | 9.03 |
| 5d | Naphthalene | | | 0.1 mol | 16.0 | 100.0 | 92.03 | 7.23 |
| 5e | 1-Naphthoic acid | | | | | 89.79 | 84.91 | 4.88 |
| 5f | (4-Ethyl)biphenyl | | | | | 75.47 | 67.45 | 6.43 |
| 5g | Bis(4-$^{tert}$butyl)biphenyl | | | | | 58.50 | 51.48 | 5.68 |
| 5h | Naphthalene | | 25 | | 18.0 | 100.0 | 91.80 | 6.78 |
| | | | | | 40.0 | | 83.39 | 7.12 |
| | | | | | 96.0 | | 87.03 | 6.95 |
| 5i | Naphthalene | 1.4 | 45 | | 18.0 | | 93.23 | 6.77 |
| 5j | | 25.0 | | | | | 91.74 | 7.20 |
| 5k | | 0.10 | | | | 71.46 | 63.39 | 5.41 |
| 5l | | 0.50 | | | | 94.62 | 85.36 | 5.49 |

Example 3:

TABLE 6

Na-(Aryl/alkyl)Naphthelide Reduction of tris[3,5-xylyl]Phosphine to Sodium bis[3,5-xylyl]Phosphide.

| | | | Conditions | | | Results | | |
|---|---|---|---|---|---|---|---|---|
| Run | Additive | Mol % | Solvent | Cosolvent | Temp. | Time (hrs.) | % Conv. | Mol % $Ar_2PNa$ | Mol % Byproduct |
| 1 | Naphthalene | 5.0 | THF | 1,2-DME | 55° C. | 3.5 | 15.2 | 15.2 | 0 |
| | | | 90 vol % | 10 vol % | | 18 | 94.3 | 79.7 | 14.8 |
| | Anthracene | | | | | 3.5 | 0 | 0 | 0 |
| | | | | | | 18 | 0 | 0 | 0 |
| 2 | Naphthalene | 5.0 | THF | 1,2-DME | 55° C. | 16 | 61.6 | 58.9 | 2.7 |
| | (4-Et)Biphenyl | | 90 vol % | 10 vol % | | | 4.2 | 4.2 | 0 |
| 3 | Biphenyl | 5.0 | THF | 1,2-DME | 55° C. | 16 | 24.8 | 24.1 | 0.7 |
| | (9-Ph)Anthracene | | 90 vol % | 10 vol % | | | 0 | 0 | 0 |
| 4 | (1-Ph)Naphthalene | 5.0 | THF | 1,2-DME | 55° C. | 2 | 0 | 0 | 0 |
| | | | 90 vol % | 10 vol % | | 22 | 49.2 | 45.3 | 3.9 |
| | | | | | | 72 | 51.4 | 48.8 | 2.6 |
| 5 | (1-Me)Naphthalene | 5.0 | THF | — | 55° C. | 18 | 88.8 | 88.8 | 0 |
| | (2-Me)Naphthalene | | | | | | 82.5 | 82.5 | 0 |
| | (1-Ph)Naphthalene | | | | | | 73.7 | 73.7 | 0 |
| 6 | (2-Me)Naphthalene | 5.0 | (2-Me)THF | — | 55° C. | 18 | 2.9 | 2.9 | 0 |
| | | 5.0 | 1,4-Dioxane | — | | | 0 | — | — |

Example 3:

See Method 2). C). in the Experimental section. Table 7 shows that the polymer supported variants also catalyze the reduction of the tris(3,5-xylyl)phosphine (3,5-TXP) to the corresponding phosphide 3,5-BXPNa, although with a lower efficiency than the small molecule, non-polymer variants listed. The column mol % Nap. Indicates how much of the respective catalyst was charged to the reaction. The reaction Time (hrs.) indicates when the reaction was stopped. The Mol % column indicates the mol % conversion of the 3,5-TXP to the 3,5-BXPNa salt (It's sort of a yield, but it was not isolated). The last column of [% Conv.]/([mol % Nap][hr.]) is basically a crude screen of naphthenic catalyst efficiency. Note the table lists in order Small molecules, homopolymer supported naphthenic catalysts, and then the synthesized random copolymer supported naphthenic catalysts. The various polymeric variant structures are as indicated above Table 1. The polymer variants, although they can catalyze reduction, are less efficient at doing so compared to the small molecule analogs. Mass transfer and kinetics are better for the small molecules. The benefit of using the polymeric variants is that they may be more easily separated from the desired product via simple alcohol precipitation for cases where the small molecule is difficult to do so or appears to co-crystallize with the desired product. Since the polymeric variants precipitate, they can also be recovered and reused rendering them recyclable and potentially green in nature.

TABLE 7

Evaluation of Small Molecule and Random (Co)polymeric Naphthenics as 3,5-TXP Reduction Catalysts.[1]

| Run | Naphthenic Catalyst | Source | Mol % Nap. | Time (hrs.) | Mol % $(3,5\text{-xylyl})_2PNa$ | [% Conv.]/[mol % Nap-hr] |
|---|---|---|---|---|---|---|
| | | Small Molecules | | | | |
| 7a | [1-methyl]naphthalene | Alfa Aesar | 5.4 | 18 | 88.82 | 0.91 |
| 7b | [2-methyl]naphthalene | | | | 82.46 | 0.85 |
| 7c | [1-phenyl]naphthalene | | | | 73.80 | 0.76 |
| | | Homopolymers | | | | |
| 7d | P[1-VNp] | Aldrich[2] | 4.6 | 18 | 19.9 | 0.24 |
| 7e | P[1-VNp] | | 25.6 | 18 | 31.1 | 0.067 |
| | | | | 72 | >99 | NA |
| 7f | P[1-VNp] | | 5.0 | 18 | 24.9 | 0.28 |
| 7g | P[2-VNp] | | 5.0 | 18 | 0 | 0 |
| | | | | 42 | 3.6 | 0.017 |
| | | | 25.0 | 18 | 8.2 | 0.018 |
| | | | | 42 | 35.0 | 0.033 |
| 7h | P[4-[1-$NpCH_2CH_2OCH_2$]St] | CRP | 3.8 | 16 | 18.3 | 0.30 |
| | | | | 40 | 61.7 | 0.40 |
| | | Copolymers | | | | |
| 7i | PSt-co-P[2-VNp][5] | Emulsion[3] | | 18 | 0 | 0 |
| 7j | PSt-co-P[4-[1-$NpCH_2OCH_2$]St-co-4-CMS][6] | CRP[4] | 8.8 | 16 | 0 | 0 |
| | | | | 40 | 61.32 | 0.17 |
| 7k | PSt-co-P[4-[1-$NpCH_2OCH_2$]St-co-4-CMS | | 1.8 | 18 | 23.7 | 0.73 |
| | | | | 88 | 100 | 0.25 |
| 7l | PSt-co-P[4-[1-$NpCH_2CH_2OCH_2$]St] | | | 18 | 17.23 | 17.23 |

TABLE 7-continued

Evaluation of Small Molecule and Random (Co)polymeric Naphthenics as 3,5-TXP Reduction Catalysts.[1]

| Run | Naphthenic Catalyst | Source | Mol % Nap. | Time (hrs.) | Mol % (3,5-xylyl)$_2$PNa | [% Conv.]/[mol % Nap-hr] |
|---|---|---|---|---|---|---|
| 7m | PSt-co-P[4-[1-NpCH$_2$CH$_2$OCH$_2$]St] | | 7.8 | 16 | 42.0 | 0.34 |
| 7n | PSt-co-P[4-[1-NpCH$_2$CH$_2$OCH$_2$]St]-co-DVB | | 4.2 | 64 | 83.3 | 0.31 |
| 7o | | | | 18 | 33.7 | 0.45 |
| 7p | PSt-co-P[4-[1-NpCH$_2$CH$_2$OCH$_2$]St] | | 1.9 | 18 | 18.9 | 0.55 |
| | | | 3.8 | | 26.5 | 0.39 |

Notes:
[1] All runs were 0.18M 3,5-TXP of in THF except for the two runs of 13069-45.
[2] The polymeric catalysts P[1-VNp] and P[2-VNp] had molecular weights of (M$_n$). = 30k and 20k, respectively.
[3] Emulsion indicates the copolymer was prepared using emulsion polymerization techniques.
[4] CRP indicates the (co)polymer was prepared by Controlled Radical Polymerization using BlocBuilder ® as the initiator.
[5] The monomer composition of the copolymer for Run 13002-164 could not easily be determined by $^1$H and $^{13}$C NMR, but was approximated from the monomer feed ratio of 9:10 for styrene:(2-vinyl)naphthalene. Polymer prepared on 13002-151.
[6] The monomer composition of the de facto terpolymeric naphthalene catalyst used in runs 13069-[4 and 7] was styrene:[4-ClCH$_2$]styrene:[4-[1-naphthylCH$_2$CH$_2$OCH$_2$]styrene] as measured by $^1$H NMR is 0.80:0.138:0.062, i.e. 6.2 mol % naphthalene-bearing monomer unit. The polymeric catalyst was prepared by post-functionalization of a 0.80:0.20 styrene:[4-ClCH$_2$]styrene random copolymer prepared by CRP, i.e. post-functionalization with the napthylethoxide anion was only about 30% complete.

Example 4:

Table 8 shows that basically the small molecule and the polymer supported naphthenic catalysts can be combined to reduce the overall charge of each individual component. Note the charge of the Co-catalyst (small molecule) is much lower than that indicated in Table 7 above. Take (1-Me)Nap Run Se below where 3.8 mol % naphthenic is in the copolymer used along with 0.1 mol % of (1-Me)Nap co-catalyst to give a % reduction of 43.5% in 18 hrs. versus 26.5% reduction in the absence of the small molecule co-catalyst (Table 7, Run 7p) and efficiency of reduction values of 0.62 versus 0.39. While not being bound to any particular theory, it is hypothesized that the small molecule co-catalyst (1-Me)Nap serves as a shuttle between the sodium metal surface and the polymer supported naphthenic units to enrich the polymer in sodium naphthalide for triaryl phosphine reductions. The exchange of sodium between free and sodium bound napthenics is fast compared to the rate of triarylphosphine reduction. Therefore, the small molecule, in some small percentage, can have a significant affect on the overall rate since it will quickly "shuttle the sodium atom (Na++e−) around all the naphthenic units, whether small molecule or polymer supported. The rate of diffusion and contact between the solid sodium surface and sterically-hindered polymer supported naphthenics is unfavorable and manifests itself in a lower overall efficiency of phosphine reduction compared to the small molecule analogs. Therefore, one may think of the small molecule co-catalyst added as an electron (e−) shuttle between the sodium surface and the sterically-hindered polymer supported naphthenics. By combining the two in the ratios indicated, one may take advantage of their respective positive attributes of high rate of reduction with case of (physical) separation via precipitation.

TABLE 8

Addition of [1-Methyl]naphthalene as a Co-catalyst of SNC Catalyzed Reductions of 3,5-TXP.

| | | Naphthenic | | | | | |
|---|---|---|---|---|---|---|---|
| | | Supported | | Co-catalyst | | Mol % | [% Conv.]/ |
| Run | Identity | | Mol % | Identity | Mol % | Time (hrs.) | (3,5-xylyl)$_2$PNa | [mol % Nap-hr] |
| 8a | PSt-co-P[4-[1-NpCH$_2$CH$_2$OCH$_2$]St] | | 3.8 | [1-Me]Nap | 0.25 | 18 | 35.43 | 0.49 |
| | | | | Styrene | 0.25 | | 26.66 | 0.37 |
| 8b | PSt-co-P[4-[1-NpCH$_2$CH$_2$OCH$_2$]St] | | 3.8 | [1-Me]Nap | 0 | 18 | 17.23 | 0.25 |
| 8c | | | | | 0.5 | | 33.67 | 0.44 |
| | | | | | 1.0 | | 41.19 | 0.48 |
| | | | | | 2.0 | | 88.34 | 0.85 |
| 8d | PSt-co-P[4-[1-NpCH$_2$CH$_2$OCH$_2$]St]-co-DVB | | 4.2 | | 0 | | 33.73 | 0.45 |
| | | | | | 0.1 | | 24.26 | 0.31 |
| | | | | | 0.25 | | 30.24 | 0.38 |
| | | | | | 0.5 | | 38.40 | 0.45 |
| 8e | PSt-co-P[4-[1-NpCH$_2$CH$_2$OCH$_2$]St]-co-DVB | | 4.2 | | 1.0 | | 39.90 | 0.43 |
| | PSt-co-P[4-[1-NpCH$_2$CH$_2$OCH$_2$]St] | | 3.8 | | 0.1 | | 43.55 | 0.62 |

What is claimed is:

1. A catalytic dispersion for the reduction of a triarylphosphines comprising one or more alkali metal dispersed in a polycyclic aromatic hydrocarbon, wherein said polycyclic aromatic hydrocarbon is at least one of a small molecule alkylated naphthenic, and a polymer supported naphthenic.

2. The catalytic dispersion of claim 1, wherein said alkali metal is sodium.

3. The catalytic dispersion of claim 1, wherein the alkali metal is a mixture of sodium and potassium.

4. The catalytic dispersion of claim 1 comprising from 5 to 45 weight % of the alkali metal based on the weight of the naphthenic component.

* * * * *